US005858738A

United States Patent [19]
Lingham et al.

[11] Patent Number: 5,858,738
[45] Date of Patent: Jan. 12, 1999

[54] ERMOPHILANE SESQUITERPENOIDS AS HIV INTERGRASE INHIBITORS

[75] Inventors: Russell B. Lingham, Watchung; Jon David Polishook, Cranford; Ali Shafiee, Westfield; Keith C. Silverman, Somerset; Sheo Bux Singh, Edison; Deborah L. Zink, Manalapan, all of N.J.

[73] Assignee: Merck & Co., Inc., Rahway, N.J.

[21] Appl. No.: 964,081

[22] Filed: Nov. 4, 1997

Related U.S. Application Data

[60] Provisional application No. 60/029,886, Nov. 7, 1996.

[51] Int. Cl.$^6$ ................ C12P 7/62; C12P 7/26; A01N 37/00; C07C 69/52; C07C 49/00; C07C 47/00

[52] U.S. Cl. .............. 435/135; 435/148; 514/510; 560/225; 568/303; 568/420

[58] Field of Search ............................ 435/135, 148, 435/171, 254.1; 514/510, 675, 695; 560/1, 129, 205, 225; 568/303, 420

[56] References Cited

U.S. PATENT DOCUMENTS 5,759,842  6/1998  Dombrowski et al. .............. 435/252.1

FOREIGN PATENT DOCUMENTS 2306476A  7/1997  United Kingdom .
96/28443  9/1996  WIPO .

OTHER PUBLICATIONS

Zhao et al. "Six new eremophilane derivatives from two *Ligularia species*," J. Nat. Prod. (Dec. 1994) 57(12): 1626–30.

Gant et al. "Oxazoline–mediated synthesis of the *Gossypium sesquiterpene* lacinilene C–7 methyl ester and a structurally related HIV–1 reverse–transcriptase inhibitor," Tetrahedron Lett. (1993) 34(23): 3707–10.

Alam et al. "Substituted naphthalenones as a new structural class of HIV–1 reverse transcriptase inhibitors," Antiviral Res. (1993) 22: 131–141.

Zdero et al. "Eremophilanolides, eudesmanolides, guianolides and other constituents from *Ondetia lineraris*," Phytochem. (1989) 28(6):1653–60.

LaFemina et al., Antimicrobial Agents & Chemotherapy, vol. 39(2), pp. 320–324 (1995), "Inhibition of human immunodeficiency virus integrase by bis–catechols".

Cushman et al., J. Med. Chem., vol. 38 (1995), pp. 443–452, "Cosalane analogues with enhanced potencies as inhibitors of HIV–1 protease and integrase".

Mazumder et al., Biochemistry, vol. 34 (1995), pp. 15111–15122, "Effects of tyrphostins, protein kinase inhibitors, on human immunodeficiency virus type 1 integrase".

Mazumder et al., J. Med. Chem., vol. 39 (1996), pp. 2472–2481, "Antiretroviral agents as inhibitors of both human immunodeficiency virus type 1 integrase and protease".

Mazumder et al., Molecular Pharmacology, vol. 49 (1996), pp. 621–628, "Effects of nucleotide analogues on human immunodeficiency virus type 1 integrase".

Kusumoto et al., C.A. 120(19):238888s, "A comparative study on the inhibitory effects of flavonoids and alkaloids on reverse transcriptases of different retroviruses" (1994).

Mazumder et al., AIDS Research and Human Retroviruses, vol. 11(1), pp. 115–125 (1995), "Inhibition of human immunodeficiency virus type 1 integrase by a hydrophobic cation . . . ".

Mazumder et al., Proc. Nat'l Acad. Sci. USA, vol. 91, pp. 5771–5775 (1994), "Inhibition of human immunodeficiency virus type 1 integrase by 3'–azido–3'–deoxythymidylate".

Carteau et al., Archives of Biochemistry & Biophysics, vol. 305(2), pp. 606–610 (1993), "Inhibitory effect of the polyanionic drug suramin on the in vitro HIV DNA integration reaction".

Fesen et al., Proc. Nat'l Acad. Sci. USA, vol. 90 (1993), pp. 2399–2403, "Inhibitors of human immunodeficiency virus integrase".

Farnet et al., Proc. Nat'l Acad. Sci. USA, vol. 93 (1996), pp. 9742–9747, "Differential inhibition of HIV–1 preintegration complexes and purified integrase protein by small molecules".

Lutzke et al., Proc. Nat'l Acad. Sci. USA, vol. 92 (1995), pp. 11456–11460, "Identification of a hexapeptide inhibitor of the human immunodeficiency virus integrase protein by using a combinatorial chemical library".

Ojwang et al., Antimicrobial Agents & Chemotherapy, vol. 39(11), pp. 2426–2435 (1995), "T30177, an oligonucleotide stabilized by an intramolecular guanosine octet, is a potent inhibitor . . . ".

Eich et al., J. Med. Chem., vol. 39 (1996), pp. 86–95, "(–)–Arctigenin as a lead structure for inhibitors of human immunodeficiency virus type–1 integrase".

Robinson, Jr., et al., Proc. Nat'l Acad. Sci. USA, vol. 93 (1996), pp. 6326–6331, "Inhibitors of HIV–1 replication that inhibit HIV integrase".

PRNewswire, Sep. 17, 1996, "Aronex reports results for lead anti–HIV integrase inhibitor compound".

Neamati et al., "Design and discovery of HIV–1 integrase inhibitors", DDT 2(11) (1997), pp. 487–498.

(List continued on next page.)

*Primary Examiner*—Jon P. Weber
*Assistant Examiner*—Susan Hanley
*Attorney, Agent, or Firm*—Catherine D. Fitch; Melvin Winokur

[57] ABSTRACT

Natural products such as certain ermophilane sesquiterpenoids and derivatives thereof are described. These compounds are useful in the inhibition of HIV integrase, the prevention or treatment of infection by HIV and the treatment of AIDS, either as compounds, pharmaceutically acceptable salts, pharmaceutical composition ingredients, whether or not in combination with other antivirals, immunomodulators, antibiotics or vaccines. Methods of treating AIDS and methods of preventing or treating infection by HIV are also described. The fungal culture MF6254, Xylaria sp. (ATCC 74397) is also described and disclosed.

13 Claims, No Drawings

OTHER PUBLICATIONS

Hazuda et al., Nucleic Acids Research, vol. 22 (6), pp. 1121–1122 (1994), "A novel assay for the DNA strand–transfer reaction of HIV–1 integrase".

Burke et al., J. Med. Chem., vol. 38 (1995), pp. 4171–4178, "Hydroxylated aromatic inhibitors of HIV–1 integrase".

Hazuda et al., J. of Virology, vol. 71(1), pp. 807–811 (1997), "Equivalent inhibition of half–site and full–site retroviral strand transfer reactions by structurally diverse compounds".

Fesen et al., Biochemical Pharma., vol. 48(3), pp. 595–608 (1994), "Inhibition of HIV–1 integrase by flavones, caffeic acid phenethyl ester (cape) and related compounds".

ERMOPHILANE SESQUITERPENOIDS AS HIV INTERGRASE INHIBITORS

This application claims benefit of priority to U.S. Ser. No. 60/029,866, filed on Nov. 7, 1996.

BACKGROUND OF THE INVENTION

A retrovirus designated human immunodeficiency virus (HIV) is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is the insertion by virally-encoded integrase of proviral DNA into the host cell genome, a required step in HIV replication in human T-lymphoid cells. Integration is believed to occur in three stages: cleavage of two nucleotides from the 3' termini of the linear proviral DNA; covalent joining of the recessed 3' OH termini of the proviral DNA at a staggered cut made at the host target site; repair synthesis by host enzymes.

Nucleotide sequencing of HIV shows the presence of a pol gene in one open reading frame [Ratner, L. et al., *Nature*, 313, 227 (1985)]. Amino acid sequence homology provides evidence that the pol sequence encodes reverse transcriptase, an integrase and an HIV protease [Toh, H. et al., *EMBO J.* 4, 1267 (1985). Power, M. D. et al., *Science*, 231, 1567 (1986); Pearl, L. H. et al., *Nature* 329, 351 (1987)].

It is known that some antiviral compounds act as inhibitors of HIV and are effective agents in the treatment of HIV and similar diseases, e.g., azidothymidine or AZT. Applicants demonstrate that the compounds of this invention are inhibitors of HIV integrase, by inhibiting strand transfer and cleavage activity. The particular advantage of the present invention is specific inhibition of HIV integrase.

Applicants have discovered that certain ermophilane sesquiterpenoid esters are potent inhibitors of HIV integrase. These compounds are useful for the treatment of AIDS or HIV infections.

BRIEF DESCRIPTION OF THE INVENTION

Compounds of formula I, as herein defined, are disclosed. These compounds are useful in the inhibition of HIV integrase, the prevention of infection by HIV, the treatment of infection by HIV and in the treatment of AIDS and/or ARC, either as compounds, pharmaceutically acceptable salts or hydrates (when appropriate), pharmaceutical composition ingredients, whether or not in combination with other antivirals, anti-infectives, immunomodulators, antibiotics or vaccines. Methods of treating AIDS, methods of preventing infection by HIV, and methods of treating infection by HIV are also disclosed.

The compounds of formula I are obtained from the fermentation of the novel fungal culture MF6254, Xylaria sp. (ATCC 74397), which is also described and disclosed.

DETAILED DESCRIPTION OF THE INVENTION AND PREFERRED EMBODIMENTS

This invention is concerned with compounds of formula I, combinations thereof, or pharmaceutically acceptable salts thereof, in the inhibition of HIV integrase, the prevention or treatment of infection by HIV and in the treatment of the resulting acquired immune deficiency syndrome (AIDS).

Compounds of formula I are defined as follows:

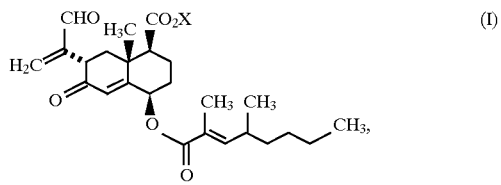
(I)

wherein X is H, $C_{1-4}$ alkyl, $C_{1-4}$ alkyl substituted with a substituent selected from
(a) phenyl, and
(b) phenyl substituted with methyl, methoxy, halogen, or hydroxy; or a pharmaceutically acceptable salt thereof.

One embodiment of the present invention is directed to compound (A):

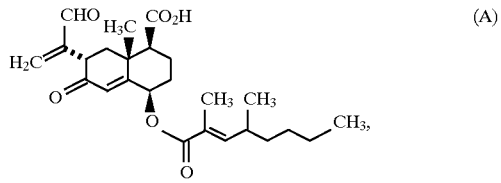
(A)

or a pharmaceutically acceptable salt thereof.

Also covered by the present invention are pharmaceutical compositions useful for inhibiting HIV integrase, comprising an effective amount of a compound of this invention. Pharmaceutical compositions useful for treating infection by HIV, or for treating AIDS or ARC, are also encompassed by the present invention, as well as a method of inhibiting HIV integrase, and a method of treating infection by HIV, or of treating AIDS or ARC. This invention also discloses the culture MF 6254, Xylaria sp. (ATCC 74397).

The present invention also relates to the preparation of compounds of structural formula I comprising:
(a) fermenting a culture of MF 6254, Xylaria sp. (ATCC 74397) to produce a fermentation broth,
(b) extracting the fermentation broth with an organic solvent,
(c) purifying the organic extract to obtain the compounds of structural formula (I).

When any variable (e.g., X, etc.) occurs more than one time in any constituent or in formula I, its definition on each occurrence is independent of its definition at every other occurrence. Also, combinations of substituents and/or variables are permissible only if such combinations result in stable compounds.

The compounds of the present inventions are useful in the inhibition of HIV integrase, the prevention or treatment of infection by human immunodeficiency virus (HIV) and the treatment of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by e.g., blood transfusion, exchange of body fluids, bites, accidental needle stick, or exposure to patient blood during surgery.

The compounds of this invention are useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HIV integrase, e.g., by competitive inhibition. Thus, the compounds of this invention are commercial products to be sold for these purposes.

Applicants have discovered that certain ermophilane sesquiterpenoids, recovered from a culture of MF6254, identified as Xylaria sp. (ATCC 74397) are useful for inhibiting HIV integrase. The compounds of formula (I) are prepared by an aerobic fermentation procedure employing a novel fungal culture MF6254 (ATCC 74397), identified as Xylaria sp., or a mutant thereof. A mutant refers to an organism in which some gene on the genome is modified, leaving the gene or genes responsible for the organism's ability to produce the compounds of formula (I) in recoverable amounts functional and heritable.

ATCC Deposit MF 6245, Xylaria, sp.

Before the U.S. filing date of the present application, on Oct. 16, 1996, a sample of MF 6254, Xylaria sp. had been deposited at the American Type Culture Collection (ATCC), 10801 University Boulevard, Manassas, Va. 20110-2209 on Oct. 16, 1996. The culture access designation is ATCC 74397. This deposit will be maintained in the ATCC for at least 30 years and will be made available to the public upon the grant of a patent disclosing it. It should be understood that the availability of a deposit does not constitute a license to practice the subject invention in derogation of patent rights granted by government action.

General Characteristics of ATCC 74397

Because of the characteristic stromata and general colony morphology, this endophytic fingus is easily placed in the genus Xylaria (Pyrenomycetes, Ascomycotina). The isolate produces no teleomorph (sexual state) or anamorph (asexual state) in culture making species identification particularly difficult. A synoptic key (Callan, B. E. and J. D. Rogers. 1992. A synoptic key to Xylaria species from continental United States and Canada based on cultural and anamorphic features. Mycotaxon 46:141–154) to twenty-three species of Xylaria based on cultural characters was employed. However, the characteristics of MF6254 do not fit well into any of the described species. Some key characters of this isolate, such as growth rate or stroma morphology, may correspond to one of the species, but the combination of the characters together do not fit well into any of the reported species. Therefore this isolate is designated simply as Xylaria sp.

MF6254 was isolated as an endophyte by the method of Bills and Polishook, 1991, as JP3770 from twigs of Aristolochia potheri (Aristolochiaceae)(155-88033) collected in Thailand. See, Bills, G. F. and J. D. Polishook.1991. Microfangi from Carpinus caroliniana. Can. J. Bot.69 (7): 1477–1482.

In the following description, all capitalized color names are from Ridgway, R.1912. Color standards and color nomenclature. Publ. by the author, Washington, D.C. 43 p.+53 pl.

On oatmeal agar (Difco) colony, with center inoculation, covering a 100 mm petri dish after 21 days at 25° C. and 67% relative humidity in 12 hr photoperiod in fluorescent light. Colony mat white, floccose with a scalloped appearance; stroma abundant, forming loose concentric rings, stout, 4–5 mm tall ×1–2 mm wide, velvety, when mature olivaceous (Deep Slate-Olive, Olivaceous Black); margin hyaline, indistinct; reverse light brown (Clay Color); exudate abundant, clear; soluble pigment absent.

On PDYA (potato-dextrose agar (Difco) w/5 g/L yeast-extract) covering the petri dish after 21d under the same inoculation and incubation conditions. Colony mat cottony, white, with 5 mm wide bands of black to olivaceous green (Deep Slate-Olive) mycelium; stroma rare, limited to inoculation point, 3–4 large, 5×3 mm, black; reverse brown (Clay Color, Tawny-Olive); exudate rare, small, clear droplets on mycelial tufts; soluble pigment absent.

On MEA (2% malt extract, Difco) covering the petri dish after 21d under the same inoculation and incubation conditions. Colony mat white, floccose to velvety, underlying a colony center dark green (Deep Slate-Olive), heavily dissected, an appearance of finger-like projections; margin, white, entire, with rare white tufts; reverse, exudate and soluble pigment absent.

No sporulation or conidiation observed. Hyphae thin walled, hyaline to dark brown, septate, 3–4 $\mu$m wide.

In general, MF 6254, Xylaria sp. (ATCC 74397) is cultured on a solid medium, or in an aqueous nutrient medium containing sources of assimilable carbon and nitrogen. For example, the cultures can be grown under submerged aerobic conditions (e.g., shaking culture, submerged culture, etc.) The, aqueous medium is preferably maintained at a pH of about 6–8 at the initiation and termination (harvest) of the fermentation process. The desired pH may be maintained by the use of a buffer such as morpholinoethane-sulfonic acid (MES), morpholinopropanesulfonic acid (MOPS), and the like, or by choice of nutrient materials which inherently possess buffering properties.

The preferred source of carbon in the nutrient medium are carbohydrates such as glucose, xylose, galactose, glycerin, starch, sucrose, dextrin, and the like. Other sources which may be included are maltose, rhamnose, raffinose, arabinose, mannose, sodium succinate, and the like.

The preferred sources of nitrogen are yeast extract, meat extract, peptone, gluten meal, cottonseed meal, soybean meal and other vegetable meals (partially or totally defatted), casein hydrolysates, soybean hydrolysates, and yeast hydrolysates, corn steep liquor, dried yeast, wheat germ, feather meal, peanut powder, distiller's solubles, etc., as well as inorganic and organic nitrogen compounds such as ammonium salts (e.g., ammonium nitrate, ammonium sulfate, ammonium phosphate, etc.), urea, amino acids, and the like.

The carbon and nitrogen sources, though advantageously employed in combination, need not be used in their pure form, because less pure materials which contain traces of growth factors and considerable quantities of mineral nutrients, are also suitable for use. When desired, there may be added to the medium mineral salts such as sodium or calcium carbonate, sodium or potassium phosphate, sodium or potassium chloride, sodium or potassium iodide, magnesium salts, copper salts, cobalt salts, and the like. If necessary, especially when the culture medium foams seriously, a defoaming agent, such as liquid paraffin, fatty oil, plant oil, mineral oil or silicone may be added.

As to the conditions for the production of cells in massive amounts, submerged aerobic cultural conditions is one method of culturing the cells. For the production in small amounts, a shaking or surface culture in a flask or bottle is employed. Furthermore, when the growth is carried out in large tanks, it is preferable to use the vegetative forms of the organism for inoculation in the production tanks in order to avoid growth lag in the process of production. Accordingly, it is desirable first to produce a vegetative inoculum of the organism by inoculating a relatively small quantity of culture medium with spores or mycelia of the organism produced in a "slant" and culturing said inoculated medium, also called the "seed medium", and then to transfer the cultured vegetative inoculum aseptically to large tanks. The fermentation medium, in which the inoculum is produced, is generally autoclaved to sterilize the medium prior to inoculation. The pH of the medium is generally adjusted to about 6–7 to the autoclaving step.

Agitation and aeration of the culture mixture may be accomplished in a variety of ways. Agitation may be provided by a propeller or similar mechanical agitation equipment, by revolving or shaking the fermentor, by various pumping equipment, or by the passage of sterile air through the medium. Aeration may be effected by passing sterile air through the fermentation mixture.

The fermentation is usually conducted at a temperature between about 20° C. and 30° C., preferably 22°–25° C., for a period of about 14–30 days, which may be varied according to fermentation conditions and scales.

Preferred culturing/production media for carrying out the fermentation include the media as set forth in the Examples.

After growth is completed, either the whole broth or the cells, harvested by conventional methods, e.g., centrifugation and filtration, are extracted with the appropriate solvent, e.g., methylethylketone.

The product of the present invention can be recovered from the culture medium by conventional means which are commonly used for the recovery of other known substances. The substances produced may be found in either or both the cultured mycelium and broth filtrate, and accordingly can be isolated and purified from the mycelium and the filtrate, which are obtained by filtering or centrifuging the cultured broth, by a conventional method such as concentration under reduced pressure, lyophilization, extraction with a conventional solvent, such as methylene chloride or methanol and the like, pH adjustment, treatment with a conventional resin (e.g., anion or cation exchange resin, nonionic adsorption resin, etc.), treatment with a conventional adsorbent (e.g., activated charcoal, silicic acid, silica gel, cellulose, alumina, etc.), crystallization, recrystallization, and the like. A preferred method is extraction of cultured whole broth with methylethylketone, followed by filtration of the extract through filtering aid such as diatomaceous earth. The methylethylketone layer of the filtrate was separated and concentrated to dryness initially by evaporating under reduced pressure followed by lyophilization. The compounds were finally isolated either by solvent partitioning and crystallization or by preparative HPLC on reversed phase systems.

Compounds of formula (I) may be isolated from the aerobic fermentation of a culture of MF 6254, Xylaria sp. (ATCC 74397). A culture of MF 6254, Xylaria sp (ATCC 74397) is defined as substantially free of its natural soil contaminants and capable of forming compounds of structural formula (I) in recoverable amounts. The culture employed in the present invention should be free from viable contaminating microorganisms deleterious to the production of the compound of structural formula (I). A biologically pure culture of MF 6254, Xylaria sp (ATCC 74397) may also be employed.

The pharmaceutically acceptable salts of the compounds of this invention include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris (hydroxymethyl)aminomethane, and tetramethylammonium hydroxide. These salts may be prepared by standard procedures, e.g. by reacting the free acid with a suitable organic or inorganic base.

For these purposes, the compounds of the present invention may be administered orally, parenterally (including subcutaneous injections, intravenous, intramuscular, intrasternal injection or infusion techniques), by inhalation spray, or rectally, in dosage unit formulations containing conventional non-toxic pharmaceutically-acceptable carriers, adjuvants and vehicles.

The terms "administration of" and or "administering a" compound should be understood to mean providing a compound of the invention or a prodrug of a compound of the invention to the individual in need of treatment.

Thus, in accordance with the present invention there is further provided a method of treating and a pharmaceutical composition for treating HIV infection and AIDS. The treatment involves administering to a patient in need of such treatment a pharmaceutical composition comprising a pharmaceutical carrier and a therapeutically-effective amount of a compound of the present invention.

As used herein, the term "composition" is intended to encompass a product comprising the specified ingredients in the specified amounts, as well as any product which results, directly or indirectly, from combination of the specified ingredients in the specified amounts.

These pharmaceutical compositions may be in the form of orally-administrable suspensions or tablets, nasal sprays, sterile injectable preparations, for example, as sterile injectable aqueous or oleagenous suspensions or suppositories.

When administered orally as a suspension, these compositions are prepared according to techniques well-known in the art of pharmaceutical formulation and may contain microcrystalline cellulose for imparting bulk, alginic acid or sodium alginate as a suspending agent, methylcellulose as a viscosity enhancer, and sweeteners/flavoring agents known in the art. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The injectible solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these compositions may be prepared by mixing the drug with a suitable non-initiating excipient, such as cocoa butter, synthetic glyceride esters of polyethylene glycols, which are solid at ordinary temperatures, but liquefy and/or dissolve in the rectal cavity to release the drug.

The compounds of this invention can be administered orally to humans in a dosage range of 0.1 to 1000 mg/kg body weight in divided doses. One preferred dosage range is 0.1 to 200 mg/kg body weight orally in divided doses. Another preferred dosage range is 0.5 to 100 mg/kg body weight orally in divided doses. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The present invention is also directed to combinations of the HIV integrase inhibitor compounds with one or more agents useful in the treatment of AIDS. For example, the compounds of this invention may be effectively administered, whether at periods of pre-exposure and/or post-exposure, in combination with effective amounts of the AIDS antivirals, imunomodulators, antiinfectives, or vaccines, such as those in the following table.

| Drug Name | Manufacturer | Indication |
|---|---|---|
| ANTIVIRALS | | |
| AL-721 | Ethigen (Los Angeles, CA) | ARC, PGL HIV positive, AIDS |
| Recombinant Human Interferon Beta | Triton Biosciences (Almeda, CA) | AIDS, Kaposi's sarcoma, ARC |
| Acemannan | Carrington Labs (Irving, TX) | ARC (See also immunomodulators) |
| Cytovene Ganciclovir | Syntex (Palo Alto, CA) | sight threatening CMV peripheral CMV retinitis |
| d4T Didehydrodeoxythymidine | Bristol-Myers (New York, NY) | AIDS, ARC |
| ddI Dideoxyinosine | Bristol-Myers (New York, NY) | AIDS, ARC |
| EL10 | Elan Corp, PLC (Gainesville, GA) | HIV infection (See also immunomodulators) |
| Trisodium Phosphonoformate | Astra Pharm. Products, Inc (Westborough, MA) | CMV retinitis, HIV infection, other CMV infections |
| Dideoxycytidine; ddC | Hoffman-La Roche (Nutley, NJ) | AIDS, ARC |
| Novapren | Novaferon Labs, Inc. (Akron, OH) Diapren, Inc. (Roseville, MN, marketer) | HIV inhibitor |
| Peptide T Octapeptide Sequence | Peninsula Labs (Belmont, CA) | AIDS |
| Zidovudine; AZT | Burroughs Wellcome (Rsch. Triangle Park, NC) | AIDS, adv, ARC pediatric AIDS, Kaposi's sarcoma, asymptomatic HIV infection, less severe HIV disease, neurological involvement, in combination with other therapies. |
| Ansamycin LM 427 | Adria Laboratories (Dublin, OH) Erbamont (Stamford, CT) | ARC |

-continued

| Drug Name | Manufacturer | Indication |
|---|---|---|
| Dextran Sulfate | Ueno Fine Chem. Ind. Ltd. (Osaka, Japan) | AIDS, ARC, HIV positive asymptomatic |
| Virazole Ribavirin | Viratek/ICN (Costa Mesa, CA) | asymptomatic HIV positive, LAS, ARC |
| Alpha Interferon | Burroughs Wellcome (Rsch. Triangle Park, NC) | Kaposi's sarcoma, HIV in combination w/Retrovir |
| Acyclovir | Burroughs Wellcome | AIDS, ARC, asymptomatic HIV positive, in combination with AZT. |
| Antibody which neutralizes pH labile alpha aberrant Interferon in an immuno-adsorption column | Advanced Biotherapy Concepts (Rockville, MD) | AIDS, ARC |
| Indinavir | Merck (Rahway, NJ) | AIDS, ARC, asymptomatic HIV positive, also in combination with AZT. |
| Nevirapine | Boeheringer Ingleheim | AIDS, ARC (protease inhibitor) |
| Delaviridine | Pharmacia-Upjohn | AIDS, ARC (protease inhibitor) |
| Ritonavir | Abbott | AIDS, ARC (protease inhibitor) |
| Saquinavir | Hoffmann-LaRoche | AIDS, ARC (protease inhibitor) |
| Nelfinavir | Agouron Pharmaceuticals | AIDS, ARC (protease inhibitor) |
| 141 W94 | Glaxo-Wellcome | AIDS, ARC (protease inhibitor) |
| DMP-266 | DuPont-Merck Pharmaceuticals | AIDS, ARC (non-nucleoside reverse transcriptase inhibitor) |
| IMMUNO-MODULATORS | | |
| AS-101 | Wyeth-Ayerst Labs. (Philadelphia, PA) | AIDS |
| Bropirimine | Upjohn (Kalamazoo, MI) | advanced AIDS |
| Acemannan | Carrington Labs, Inc. (Irving, TX) | AIDS, ARC (See also anti-virals) |
| CL246,738 | American Cyanamid (Pearl River, NY) Lederle Labs (Wayne, NJ) | AIDS, Kaposi's sarcoma |
| EL10 | Elan Corp, PLC (Gainesville, GA) | HIV infection (See also anti-virals) |
| Gamma Interferon | Genentech (S. San Francisco, CA) | ARC, in combination w/TNF (tumor necrosis factor) |
| Granulocyte Macrophage Colony Stimulating Factor | Genetics Institute (Cambridge, MA) Sandoz (East Hanover, NJ) | AIDS |
| Granulocyte Macrophage Colony Stimulating Factor | Hoeschst-Roussel (Sommerville, NJ) Immunex (Seattle, WA) | AIDS |
| Granulocyte Macrophage Colony Stimulating Factor | Schering-Plough (Madison, NJ) | AIDS AIDS, in combination w/AZT |
| HIV Core Particle Immunostimulant | Rorer (Ft. Washington, PA) | seropositive HIV |
| IL-2 Interleukin-2 | Cetus (Emeryville, CA) | AIDS, in combination w/AZT |
| IL-2 Interleukin-2 | Hoffman-La Roche (Nutley, NJ) Immunex | AIDS, ARC, HIV, in combination w/AZT |

-continued

| Drug Name | Manufacturer | Indication |
|---|---|---|
| Immune Globulin Intravenous (human) | Cutter Biological (Berkeley, CA) | pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute (Miami, FL) | AIDS, ARC |
| Alpha-2 Interferon | Schering Plough (Madison, NJ) | Kaposi's sarcoma w/AZT: AIDS |
| Methionine-Enkephalin | TNI Pharmaceutical (Chicago, IL) | AIDS, ARC |
| MTP-PE Muramyl-Tripeptide | Ciba-Geigy Corp. (Summit, NJ) | Kaposi's sarcoma |
| Granulocyte Colony Stimulating Factor | Amgen (Thousand Oaks, CA) | AIDS; in combination w/AZT |
| rCD4 Recombinant Soluble Human CD4 | Genentech (S. San Francisco,CA) | AIDS, ARC |
| rCD4-IgG hybrids | | AIDS, ARC |
| Recombinant Soluble Human CD4 | Biogen (Cambridge, MA) | AIDS, ARC |
| Interferon Alfa 2a | Hoffman-La Roche (Nutley, NJ) | Kaposi's sarcoma AIDS, ARC, in combination w/AZT |
| SK&F106528 Soluble T4 | Smith, Kline & French Laboratories (Philadelphia, PA) | HIV infection |
| Thymopentin | Immunobiology Research Institute (Annandale, NJ) | HIV infection |
| Tumor Necrosis Factor; TNF | Genentech (S. San Francisco, CA) | ARC, in combination w/gamma Interferon |
| ANTI-INFECTIVES | | |
| Clindamycin with Primaquine | Upjohn (Kalamazoo, MI) | PCP |
| Fluconazole | Pfizer (New York, NY) | cryptococcal meningitis, candidiasis |
| Pastille Nystatin Pastille | Squibb Corp. (Princeton, NJ) | prevention of oral candidiasis |
| Ornidyl Eflornithine | Merrell Dow (Cincinnati, OH) | PCP |
| Pentamidine Isethionate (IM & IV) | LyphoMed (Rosemont, IL) | PCP treatment |
| Trimethoprim | | antibacterial |
| Trimethoprim/sulfa | | antibacterial |
| Piritrexim | Burroughs Wellcome (Rsch. Triangle Park, NC) | PCP treatment |
| Pentamidine isethionate for inhalation | Fisons Corporation (Bedford, MA) | PCP prophylaxis |
| Spiramycin | Rhone-Poulenc Pharmaceuticals (Princeton, NJ) | cryptosporidial diarrhea |
| Intraconazole-R51211 | Janssen Pharm. (Piscataway, NJ) | histoplasmosis; cryptococcal meningitis |
| Trimetrexate | Warner-Lambert | PCP |
| OTHER | | |
| Recombinant Human Erythropoietin | Ortho Pharm. Corp. (Raritan, NJ) | severe anemia assoc. with AZT therapy |
| Megestrol Acetate | Bristol-Myers (New York, NY) | treatment of anorexia assoc. w/AIDS |
| Total Enteral Nutrition | Norwich Eaton Pharmaceuticals (Norwich, NY) | diarrhea and malabsorption related to AIDS |

It will be understood that the scope of combinations of the compounds of this invention with AIDS antivirals, immunomodulators, anti-infectives or vaccines is not limited to the list in the above Table, but includes in principle any combination with any pharmaceutical composition useful for the treatment of AIDS.

Indinavir is an inhibitor of HIV protease and is the sulfate salt of N-(2(R)-hydroxy-1(S)-indanyl)-2(R)-phenylmethyl-4-(S)-hydroxy-5-(1-(4-(3-pyridyl-methyl)-2(S)-N'-(t-butylcarboxamido)-piperazinyl))-pentaneamide ethanolate, and is synthesized according to U.S. Pat. No. 5,413,999. Indinavir is generally administered at a dosage of 800 mg three times a day.

EXAMPLE 1

Fermentation

A. Media

Seed medium contained the following in g/L: corn steep liquor, 5g; tomato paste, 40; oat flour, 10; glucose, 10; agar, 4; $FeSO_4 \cdot 7H_2O$, 0.01; $MnSO_4 \cdot 4H_2O$, 0.01; $CuCl_2 \cdot 2H_2O$, 0.00025; $CaCl_2$, 0.001; $H_3BO_3$, 0.00056; $(NH_4)_6Mo_7O_{24} \cdot 4H_2O$, 0.00019; $ZnSO_4 \cdot 7H_2O$, 0.002. The pH was adjusted to 6.8.

Production media contained the following per 250 mL flask: brown rice, 10 g; base liquid, 20 mL. Base liquid contained the following in g/L: yeast extract, 1; sodium tartrate, 0.5; $KH_2PO_4$, 0.5. The flasks were autoclaved for 15 minutes at 121° C., 15 psi and stored. Prior to innoculation, 15 mL of distilled water were added per flask and the flasks were sterilized for 20 minutes at minutes at 121° C., 15 psi.

B. Innoculum Preparation

Frozen vegetative mycelia (FVM) were prepared by inoculating 50 mL of seed medium in a 250 mL flask and incubating at 25° C., 85% relative humidity and at 200 rpm for 3–5 days. Aliquots of the culture were frozen and used as a source of innoculum for future experiments.

C. Seed Culture

To 50 mL of seed media in a 250 mL flask, 2.0 mL of FVM was added as inoculum and the flasks were incubated at 25° C., 85% relative humidity and at 200 rpm for days 2–3 days.

D. Production of Culture and Extraction

To 35 mL of production media in a 250 mL flask, 1 mL of seed culture was added as innoculum and the flasks were incubated a 25° C., 85% relative humidity and at 200 rpm for days 24 days. Each flask was then extracted with 50 mL of methyl ethyl ketone and the solids were discarded.

EXAMPLE 2

Isolation of HIV Intesrase Inhibitor Compound A

Ten mL methyl ethyl ketone extract was prepared from a ten mL broth of the Xylaria sps prepared according to the fermentation procedures in Example 1, above by shaking the broth with methyl ethyl ketone for 20–30 min followed by filtration through a filtration aid. The filtrate was concentrated to dryness initially at reduced pressure on a rotatory evaporator followed by lyophilization to give a 50 mg of colorless solid. The solid was dissolved in 3 mL methanol and filtered.The filtrate was concentrated to a volume of 1.5 mL and was injected to a Zorbax$^R$ HPLC colunmn (22×250 mm). The column was eluted at a flow rate of 8 mL per min with a 50 to 80% linear gradient of acetonitrile in water over 60 min. A 220 nm in-line ultraviolet light detection was used for monitoring the elution profile in HPLC. The compound responsible for HIV integrase activity eluted between 30–35 min which upon concentration at reduced pressure followed by lyophilization gave compound A as a colorless powder.

EXAMPLE 3

Larde Scale Isolation of HIV Inteffrase Inhibitor Compound A

A 700 mL whole broth of Xylaria species as described in Example I above was extracted with 700 mL methyl ethyl ketone by shaking for ~30 minutes at room temperature. The insoluble portion of the broth was removed by filtration through a filter aid such as diatomaceous earth. The filtrate which contained all of the biological activity (as determined by employing the assay described in Examples 14 and 15) was concentrated under reduced pressure to a small volume which upon lyophilization gave a 3.8 g of crude material that contained a significant amount of Compound A.

The crude material was suspended in a 200 mL water-methanol mixture and acidified to pH 2.0 by addition of dilute hydrochloric acid. This mixture was washed with hexane (200 mL) and extracted with ethyl acetate (3×300 mL). The latter extract was dried over sodium sulfate and concentrated to dryness under reduced pressure to give a still-crude mixture of compounds weighing 3.5 g containing Compound A. The crude mixture was dissolved in 6 mL methanol and was subdivided into 3 equal portions of 2 mL each. One of the three portions was purified on a Phenomenex$^R$ primesphere (50×250 mm) HPLC column using a 60 min linear gradient of 40 to 80% acetonitrile in water (both solvents contained 0.1% trifluoroacetic acid). The column was eluted at a flow rate of 60 mL per min. The HIV integrase inhibitor Compound A eluted between 29–33 minutes. This chromatographic process was repeated with the remaining two portions of the crude mixture. The HPLC fractions containing Compound A were combined from the three chromatographic runs and was concentrated on a rotatory evaporator at reduced pressure to remove most of the acetonitrile. Subsequent lyophilization of the fraction gave Compound A as a colorless, amorphous powder.

EXAMPLE 4

Physical Properties of Compounds of Structure I

Compound A: The compound of structural formula I wherein X is hydrogen.

Mass Spectral Data:

Mass spectra were recorded on Jeol SX-102A(electron impact, EI, 90eV) and JEOL HX110 (Fast Atom Bombardment, FAB) mass spectrometers. Exact mass measurements were performed at high resolution (HR-EI) using perfluorokerosene (PFK) as an internal standard. The FAB spectrum was run in a matrix of dithiothreitoy dithioerythritol (20/80).

The molecular weight of Compound A was determined by FAB-MS and EI-MS to be 430. High resolution EI-MS indicated a molecular formula of $C_{25}H_{34}O_6$ (found 430.2370, calculated 430.2355). Critical fragment ions were observed at m/z 153 and 260.

UV

UV (MeOH) $\lambda_{max}$: 220 nm;

Optical Rotation $[\alpha]^{25}D=+38.3$ (c, 0.63, MeOH).

$^{13}C$ NMR and $^1H$ NMR

All of the NMR spectra were recorded on a Varian Unity 400 MHz spectrometers operating at a field strength of 400 MHz for proton NMR, 100 MHz for carbon NMR respectively. The data are summarized in following Table.

TABLE

NMR Assignment of Compound A in $CDCl_3$ at 25° C.

| # | δC | δH, mult, J |
|---|------|-------------|
| 1 | 196.85 | — |
| 2 | 193.13 | 9.54,s |
| 3 | 177.87 | — |
| 4 | 166.78 | — |
| 5 | 158.90 | — |
| 6 | 149.69 | 6.54, dq, 10, 1.2 |
| 7 | 147.66 | — |
| 8 | 136.47 | 6.35, s; 6.25, s |
| 9 | 129.60 | 6.10, s |
| 10 | 125.83 | — |
| 11 | 72.65 | 5.25, t, 2.8 |
| 12 | 53.31 | 2.46, dd, 13.2, 3.2 |
| 13 | 43.18 | 2.26, t, 13.6; 2.12, dd, 13.2, 4.0 |
| 14 | 43.08 | 3.73, dd, 14.8, 4.4 |
| 15 | 38.28 | — |
| 16 | 36.53 | 1.4, m; 1.3, m |
| 17 | 33.34 | 2.50, m |
| 18 | 29.77 | 2.15, m; 1.7, m |
| 19 | 29.66 | 1.2, m |
| 20 | 22.78 | 1.3, m |
| 21 | 20.12 | 2.3, m; 1.9, m |
| 22 | 19.98 | 1.00, d, 6.6 |
| 23 | 19.53 | 1.50, s |
| 24 | 14.08 | 0.87, t, 7.2 |
| 25 | 12.65 | 1.80, d, 1.6 |

EXAMPLE 5

Preparation of an Ammonium Salt

A 0.1 mmol sample of Compound A, the free acid of the compound of formula (I) is dissolved in 10 mL ethyl acetate. The resulting solution is saturated with gaseous ammonia and the ammonium salt precipitates from solution.

EXAMPLE 6

Preparation of a Potassium Salt

A solution of 0.1 mmol of Compound A, the free acid of a compound of formula (I), in 10 mL methanol is treated with an aqueous or methanolic solution containing 0.1 mmol of potassium hydroxide. Evaporation of the solvent affords the potassium salt.

In a similar fashion, the sodium and lithium salts can be formed.

EXAMPLE 7

Preparation of a Calcium Salt

A solution of 0.1 mmol of Compound A, the free acid of a compound of formula (I), in 20 mL 6:4 methanol:water is treated with an aqueous solution of 0.1 mmol of calcium hydroxide. The solvents are evaporated to give the corresponding calcium salt.

EXAMPLE 8

Preparation of an Ethylenediamine Salt

A solution of 0.1 mmol of Compound A, the free acid of a compound of formula (I), in 10 mL of methanol is treated with 0.1 mmol of ethylenediamine. Evaporation of the solvent affords the ethylenediamine salt.

The procedure can also be applied to the preparation of the N,N"-dibenzylethylenediamine salt.

EXAMPLE 9

Preparation of a Tris(hydroxymethyl)aminomethane Salt

To a solution of 0.1 mmol of Compound A, the free acid of a compound of formula (I) in 10 mL of methanol is added 0.1 mmol of tris(hydroxymethyl)aminomethane dissolved in 10 mL of methanol. Evaporation of the solvent gives a corresponding salt form.

Similarly prepared are the salts of L-ornithine, L-lysine, and N-methylglutamine.

EXAMPLE 10

Preparation of an L-arginine Salt

A solution of 0.1 mmol of Compound A, the free acid of a compound of formula (I), in 20 ml of 6:4 methanol:water is treated with an aqueous solution of 0.1 mmol of L-arginine. Evaporation of the solvent affords the title salt.

Similarly prepared are the salts of L-ornithine, L-lysine, and N-methylglutamine.

EXAMPLE 11

Preparation of the Compound of Structural Formula I wherein X is $CH_3$ (Method 1)

Compound A (0.6 mg) is dissolved in 1 mL diethyl ether and stirred at 0° C. Etheral cyanamide is added dropwise until the solution remains yellow. The solution is evaporated under a stream of nitrogen to yield the title compound.

EXAMPLE 12

Preparation of the Compound of Structural Formula I wherein X is $CH_3$

To a cooled (−78° C.) solution of Compound A (0.6 mg) in methylene chloride (0.3 mL) and methanol (0.02 mL) was added an excess solution of tetramethylsilyl diazomethane in hexane. The solution was stirred for 10 min and then quenched with a 2 drops of acetic acid. The volatile components of the reaction mixture were removed under a stream of nitrogen and the reaction product was purified on a Pasteur pipette filled with silica gel. Elution with 40% ethyl acetate in hexane gave pure methyl ester of Compound A as a gum.

Mass spectral data of methyl ester: High Resolution EI MS (m/z): 444.2502 ($M^+$, 1%, calcd. for $C_{26}H_{36}O_6$: 444.2512).

EXAMPLE 13

Preparation of the Compound of Structural Formula I wherein X is Isopropyl

A solution of 5 mg of Compound A in 0.5 mL of tetrahydrofuran (THF) is treated at room temperature with 1 equivalent of N,N'-diisopropyl-O-benzyl isourea for 18 hours. The reaction mixture is then chilled to −15° C., filtered to remove the urea. The filtrate is concentrated under reduced pressure to yield the title compound.

The method of Example 13 is also suitable for the preparation of other ester derivatives such as: 1) methyl and the other lower alkyls, and 2) substituted benzyl esters, using the appropriately substituted isourea.

EXAMPLE 14

HIV Integrase Substrate Cleavage and Integration Assay

An assay for trimming of the 3' end of HIV long terminal repeat terminus by HIV-1 integrase was conducted according to LaFemina, R. L. et al., J. Virol 10, 5624 (1991), herein incorporated by reference for these purposes. To assay inhibition of HIV integrase substrate cleavage, the reaction was conducted with inhibitor having various concentrations in the range of 0.1 to 100 μM. Results follow:

| Compound | $IC_{50}$ |
|---|---|
| A | 5–10 μM |

EXAMPLE 15

Strand Transfer Assay for HIV Integrase

A microtiter assay for ligation of processed donor (HIV) DNA to unspecific, nicked host DNA was conducted according to Hazuda, D. J. et al., Nucl. Acids, Res. 22, 1121 (1994), herein incorporated by reference for these purposes. To assay inhibition of such strand transfer by HIV integrase, the reaction was conducted with inhibition having various concentrations in the range of 0.1 to 100 μM.

Results follow.

| Compound | $IC_{50}$ |
|---|---|
| A | 5–10 μM |

EXAMPLE 16

Assay for Assembly of HIV Integrase/donor (HIV) DNA Complexes

An assay measuring the binding of HIV Integrase to immobilized donor (HIV) DNA was conducted according to Wolfe, A. L. et al., J. Virol. 70, 1424 (1996), herein incorporated by reference for these purposes. To assay inhibition of such assembly or binding, the reaction was conducted with inhibitor having various concentrations in the range of 0.1 to 100 μM. Results follow.

| Compound | $IC_{50}$ |
|---|---|
| A | 10 μM |

EXAMPLE 17

Oral Composition

As a specific embodiment of an oral composition of a compound of this invention, 50 mg of Compound A is formulated with sufficient finely divided lactose to provide a total amount of 580 to 590 mg to fill a size 0 hard gelatin capsule.

While the foregoing specification teaches the principles of the present invention, with examples provided for the purpose of illustration, it will be understood that the practice of the invention encompasses all of the usual variations, adoptions, or modifications, as come within the scope of the following claims and its equivalents.

What is claimed:
1. A compound of the formula

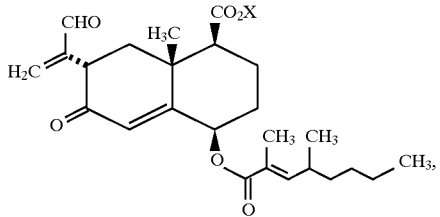

wherein X is selected from:
(1) H.
(2) $C_{1-4}$ alkyl, and
(3) $C_{1-4}$ alkyl substituted with a substituent selected from
   (a) phenyl, and
   (b) phenyl substituted with methyl, methoxy, halogen, or hydroxy;
or a pharmaceutically acceptable salt thereof.

2. The compound according to claim 1, of the structure:

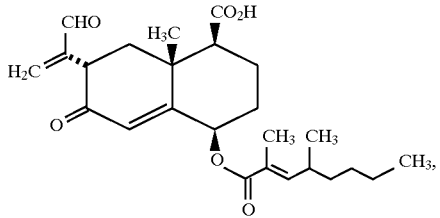

or a pharmaceutically acceptable salt thereof.

3. A compound of molecular formula $C_{25}H_{34}O_6$ and having the following properties:
   (a) the $^{13}$CNMR chemical shifts as measured in $CDCl_3$ at 25° C. at 100 MHz:196.85, 193.13, 177.87, 166.78, 158.90, 149.69, 147.66, 136.47, 129.60, 125.83, 72.65, 53.31, 43.18, 43.08, 38.28, 36.53, 33.34, 29.77, 29.66, 22.78, 20.12, 19.98, 19.53, 14.08, 12.65;
   (b) $^1$HNMR chemical shifts as measured in $CDCl_3$ at 25° C. at 400 MHz: 9.54(s), 6.54 (dq, 10, J=1.2), 6.35(s), 6.25(s), 6.10(s), 5.25 (t, J=2.8), 2.46 (dd, J=13.2, 3.2), 2.26 (t, J=13.6), 2.12 (dd, J=13.2, 4.0), 3.73 (dd, J=14.8, 4.4), 1.4 (m), 1.3 (m), 2.50(m), 2.15 (m), 1.7 (m), 1.2 (m), 1.3 (m), 2.3 (m), 1.9 (m), 1.00 (d, J=6.6), 1.50 (s), 0.87 (t, 7.2), 1.80 (d, 1.6);
   (c) an ultraviolet absorption spectrum in methanol which exhibits absorption maximum at 220 nm, and
   (d) an optical rotation of $[\alpha]^{25}D=+38.3$.

4. A pharmaceutical composition for inhibiting HIV integrase, comprising an effective amount of the compound according to claim 1, and a pharmaceutically acceptable carrier.

5. The pharmaceutical composition of claim 4, for treating infection by HIV, or for treating AIDS or ARC.

6. A pharmaceutical composition comprising a therapeutically effective amount of the compound of claim 1, in combination with a therapeutically effective amount of an AIDS treatment agent selected from
   an AIDS antiviral agent,
   an anti-infective agent; and
   an immunomodulator.

7. The composition of claim 6, wherein the antiviral agent is an HIV protease inhibitor.

8. The composition of claim 7, wherein the HIV protease inhibitor is N-(2(R)-hydroxy-1-(S)-indanyl)-2(R)-phenylmethyl-4(S)-hydroxy-5-(1-(4-(3-pyridylmethyl)-2(S)-N'-(t-butylcarboxamido)-piperazinyl))-pentaneamide or a pharmaceutically acceptable salt thereof.

9. A pharmaceutical composition made by combining the compound of claim 1 and a pharmaceutically acceptable carrier.

10. A process for making a pharmaceutical composition comprising combining the compound of claim 1 and a pharmaceutically acceptable carrier.

11. A method of inhibiting HIV integrase, comprising the administration to a mammal in need of such treatment a therapeutically effective amount of the compound of claim 1.

12. A method of treating infection by HIV, or of treating AIDS or ARC, comprising the administration to a mammal in need of such treatment a therapeutically effective amount of the compound of claim 1.

13. A process of making the compound according to claim 2, comprising cultivating MF 6254, Xylaria sp. (ATCC 74397) or a mutant thereof, under conditions suitable for the formation of said compound and recovering said compound.

* * * * *

UNITED STATES PATENT AND TRADEMARK OFFICE
CERTIFICATE OF CORRECTION

PATENT NO. : 5,858,738

DATED : 1/12/99

INVENTOR(S) : RUSSELL B. LINGHAM et al.

It is certified that error appears in the above-identified patent and that said Letters Patent is hereby corrected as shown below: On the title page and in column 1, lines 1-2; delete the title at Item 54, and substitute therefor, -- EMOPHILANE SESQUITERPENOIDS AS HIV INTEGRASE INHIBITORS -- .

In Claim 1, line 15, delete " (1) H. " and substitute therefor, -- (1) H, --.

Signed and Sealed this

Fifteenth Day of June, 1999

Attest:

Q. TODD DICKINSON

Attesting Officer     Acting Commissioner of Patents and Trademarks